United States Patent [19]

Beckley et al.

[11] Patent Number: 4,683,100
[45] Date of Patent: Jul. 28, 1987

[54] COPOLYMERIZABLE ETHYLENICALLY UNSATURATED SURFACTANTS FOR LATEX PREPARATION

[75] Inventors: Ronald S. Beckley, Gilbertsville; Rodney L. Randow, Norristown; Graham Swift, Blue Bell, all of Pa.

[73] Assignee: Rohm and Haas Company, Philadelphia, Pa.

[21] Appl. No.: 683,973

[22] Filed: Dec. 20, 1984

[51] Int. Cl.$^4$ .................. C07C 143/22; C08F 2/24
[52] U.S. Cl. ...................... 260/513 R; 525/291; 526/214
[58] Field of Search .............. 260/503, 513 R, 513 B, 260/513 T

[56] References Cited

U.S. PATENT DOCUMENTS

| | | | |
|---|---|---|---|
| 2,308,503 | 1/1943 | Farrington | 260/513 R |
| 2,316,719 | 4/1943 | Russell | 260/513 R |
| 2,344,833 | 3/1944 | Rummelsburg | 260/513 R |
| 2,393,608 | 1/1946 | Bruson . | |
| 4,097,677 | 6/1978 | Emmons et al. | 560/220 |
| 4,140,724 | 2/1979 | Nyi et al. | 568/665 |

*Primary Examiner*—Christopher Henderson
*Attorney, Agent, or Firm*—Carl W. Battle; Douglas E. Winters; Michael B. Fein

[57] ABSTRACT

Disclosed herein are compounds of the formula

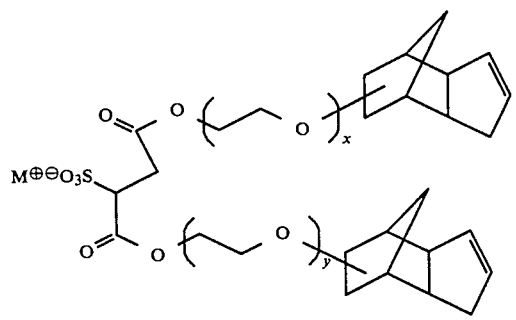

wherein M is a cation selected from the group consisting of alkali metal, ammonium, amino, and hydrogen; and wherein x and y are independently selected from 0 to 2.

These compounds are disclosed as being useful as graftable and/or copolymerizable surfactants in latex preparation.

4 Claims, No Drawings

COPOLYMERIZABLE ETHYLENICALLY UNSATURATED SURFACTANTS FOR LATEX PREPARATION

BACKGROUND OF THE INVENTION

1. Field of the Invention

This invention relates to novel surfactants for emulsion polymerization for control of latex particle size and stability.

2. Description of Prior Art

While surfactants are widely used in emulsion polymerizations, for most subsequent applications in coatings, adhesives, binders and the like, their presence is detrimental. They may contribute negatively to water resistance, adhesion, corrosion resistance, and block resistance of the film, and frequently also increase the tendency to foam, and affect the capability and stability of the latex in its formulations.

The use of ultrafine latexes has been an important advantage in latex coating technology and often can impart the important properties of chalk adhesion, better film formation and water resistance. The conventional method of making such ultrafine latexes, however, requires large amounts of surfactant because of the large latex particle surface area. Therefore, the improvement due to ultrafine latexes can be transitory and lost on aging formulation, heating, or a combination of these. Presumably, the surfactant equilibrates with the surfaces of all the materials in the formulation.

Various polymerizable surfactants have been described in the literature and are available commercially. One such series of surfactant is described in U.S. Pat. No. 4,049,608 to Steckler et al. However, the Steckler et al surfactants suffer from the disadvantage of only having two allylic protons per molecule. Some other commercial surfactants have relatively reactive graft sites, such as allylesters and maleates. The problem with most of the prior polymerizable surfactants is that virtually all of them have the reactive group in the wrong end of the soap molecule.

SUMMARY OF THE INVENTION

It is an objective, therefore, of the present invention to provide polymerizable surfactants which efficiently control the latex particle size. It is another object to provide surfactant compounds which produce latexes having low foam tendencies, low water sensitivity in dried film, improved block resistance, and improved latex stability. A further object is to provide a method of using such surfactants, especially in emulsion polymerizations of one or more unsaturated monomers.

These objects and others which will become apparent from the following disclosure are achieved by the present invention which comprises compounds of the formula

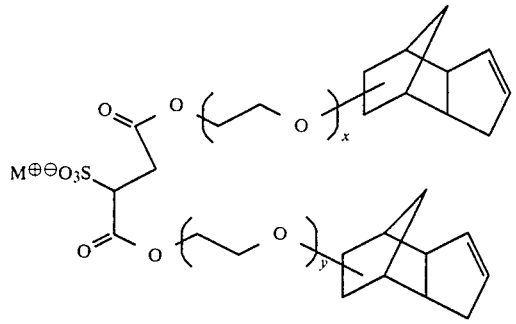

wherein M is a cation selected from the group consisting of alkali metal, ammonium, amino, and hydrogen; and wherein x and y are independently selected from 0 to 2.

DETAILED DESCRIPTION OF THE INVENTION AND THE PREFERRED EMBODIMENTS

The compounds of the invention are prepared by reaction of dicyclopentadiene and, depending on the value of x and y, either water, ethylene glycol, diethylene glycol, or mixtures thereof. The resultant tricyclo [5.2.1.0$^{2,6}$]dec-3-en-(8 or 9 oxyethyl)$_n$ alcohol (wherein n equals 0 to 2) is then reacted with maleic anhydride to form the disubstituted maleate which is, in turn, reacted with bisulfite ion to form the compounds of the invention. A preferred method is when n=0 and dicyclopentenyl formate is transesterified with dialkyl maleate or fumarate.

The compounds are useful as graftable and/or copolymerizable surfactants with unsaturated comonomers. The most frequently used comonomers are acrylates, methacrylates, styrenes, acrylonitriles, vinyl alkanoates, and butadienes.

In an emulsion copolymerization the amount of the surfactant compound of the invention useful is generally about 0.5 to 5% by weight (based on monomer) with preferred amounts being 0.5 to 3%, and more preferably from about 1 to about 3%. The particle size of the latex made by the process of the invention is generally about 40 to 200 nanometers and more preferably in the ultrafine range of about 50 to about 110 nanometers.

The resultant latexes are useful for paint, coatings, adhesives, roof mastics, calks, non-woven binders, and the like, i.e., wherever the latexes are useful.

One advantage of the present invention is improved latex stability because the surfactant cannot be extracted by other materials in the formulation. Further, the resultant latexes have improved low foaming tendencies, lower water sensitivity in the dried film, and improved block resistance.

The following examples illustrate a few embodiments of the invention. These examples are meant to be merely illustrative and are not intended to be limiting.

EXAMPLES

1. A dried, 2-1, 4-neck round-bottom flask fitted with thermometer, addition funnel, stirrer and condenser was charged with 392 g (4 mol) of maleic anhydride (freshly pulverized briquette). With the starting materials at room temperature and with stirring, about one fourth of the 777.2 g (4 mol) charge of tricyclo[5.2.1.0$^{2,6}$]dec-3-en(8 or 9) oxyethyl alcohol (1) was added. The remaining 1 was then added over about 1 hr and then heated to 50 C. After heating at about 50 C. for 19 h, the conversion was found to be about 87%. MEHQ (0.12 g) was added and the reaction was heated at about 70–77 C. for an additional 6 h. Final conversion was 91%. The reaction mixture was monitored by nmr for conversion. The adduct has a singlet at delta 6.85 ppm (2 H, HC=CH) and unreacted maleic anhydride has a singlet at delta 7.3 ppm (2H) ppm. The product produced was tricyclo[5.2.1.0$^{2,6}$]dec-3-en-(8 or 9) oxyethyl maleate (2).

2. A 500-ml, 3-necked, round-bottom flask fitted with Dean-Stark trap, condenser, stirrer and thermometer was charged with 146 g (0.5 mol) 2, 97 g (0.5 mol) 1 and 125 g toluene. After the solution was well mixed, 1.5 g of concentrated sulfuric acid was added. The reaction was heated to reflux (110–132 C.) and 8.1 ml (0.45 mol) of water was separated in the Dean-Stark trap. The cooled reaction was extracted successively with water, 10% sodium carbonate solution and brine. Emulsion formed readily and long times were necessary to get adequate separation. The washed organic layer was diluted with toluene and dried over magnesium sulfate (anhyd). The toluene was removed from the product by evaporation at temperatures up to 100 C. on a rotary evaporator.

The product retained 1.7% toluene. The nmr spectra of the product is consistent with the desired diester, which was di-(tricyclo[5.2.1.0$^{2,6}$]dec-3-en(8 or 9) oxyethyl) maleate (3).

3. A 500-ml, 3-necked, round-bottom flask fitted with a stirrer, thermometer, and condenser was charged with 187.2 g (0.4 mol) 3, 43.7 g (0.42 mol) sodium metabisulfite, and 40 g water. An outlet hose from the condenser terminated in about 1.5" silicon oil to create a slight positive pressure. The reaction was heated to about 90 C. and within about 2 h had exothermed slightly to 100 C. and then cooled to 95 C. During this time the reaction mixture became homogeneous, clear and soluble in water. About 25 mg of MEHQ was added to the product. The resulting product, sodium di-(tricyclo[5.2.1.0$^{2,6}$]dec-3-en(8 or 9) oxyethyl) sulfosuccinate (4), was clear, homogeneous, dark brown and had a slight odor of sulfur dioxide.

4. By modifying Examples 2 and 3, starting with the monoester 2 and various alcohols, a series of mixed sulfosuccinate soaps each bearing an average of one tricyclodecenyl moiety were prepared. Since the step to prepare the diester is strong acid catalyzed, the actual product is expected to be a mixture of the all possible diester maleates including the dicyclic diester. (Fumerates might also formed in any of the reactions, but after addition of the bisulfite it also yields the sulfosuccinate). In this way, mixed diester sulfosuccinates with one ester=ethyl, butyl, octyl, Carbitol and butyl Carbitol were prepared.

5. (Comparative) Sodium di(tricyclo[5.2.1.0$^{2,6}$]decan-8-oxyethyl) sulfosuccinate (6), which was the saturated analog, was prepared as follows:

A pressure vessel was charged with 58 g (0.3 mol) of alcohol 1, 300 g ethyl alcohol (3A) and platinum dioxide (small spatula). The mixture was hydrogenated on a Parr apparatus with between 44–20 lb. hydrogen pressure. The reaction was rapid, taking up an estimated 0.3 mol in half an hour. The solution was filtered on Hyflo Super Cel and the filtrate treated with activated charcoal and filtered on glass fiber paper to give a pinkish solution. The ethanol was evaporated on a rotary evaporater to give a brownish oil. The product was distilled through a 4" vigreaux column giving a single fraction (88–92 C./0.13 mm) of a clear, viscous liquid. Distilled yield of 5 was 90% The nmr spectrum was consistent with the expected product.

The saturated alcohol 5 was used in reactions analogous to Examples 1, 2, and 3 to prepare the saturated product 6. In this instance, the reaction analogous to Examples 1 and 2 were combined in a single step.

6. Sodium Di-(tricyclo[5.2.1.0$^{2,6}$]dec-3-en-(8 or 9)-yl sulfosuccinate (9), the analog of 4 without the ethyleneglycol bridge, was prepared from the formate by transesterification as described stepwise in Examples 7, 8 and 9.

7. Preparation of Tricyclo[5.2.1.0$^{2,6}$]dec-3-en-(8 or 9)-yl formate (7).

A 3-1, 4-necked, round-bottom flask fitted with a thermometer, stirrer, condenser, addition funnel and nitrogen inlet was charged with 613.8 g (11.7 mol) formic acid (Mallinkrodt, 88%) and 10.2 g of 98% methane sulfonic acid. The mixture was heated under nitrogen to 100–103 C. and then 1251 g (9 mol) of 95% dicyclopentadiene was added over about 1 h. The reaction was held at about 103 C. for about 4.5 h. The reaction was sampled hourly and analyzed by GLPC (0.5 m × ⅛", 5% OV 101 on Chromosorb HPG, 70 C. (1 min) programed 10 C./min to 200 C. (10 min)) The dicyclopentadiene ($t_r$=2.53 min) decreased to 0% as the product peaks ($t_r$=5.61 and 6.54 min) increased to 4.8 and 82 area % respectively.

The reaction mixture was neutralized with 11 g of sodium carbonate and then equipped with a 10-plate Oldershaw column and distillation head and vacuum distilled. The forerun (48 C./78 mm–20 C./15 mm) was hazy (water, formic acid). The product was distilled mainly at 121–122 C./16–17 mm. Total distilled yield of 7 was 1416.6 g (88%).

8. Preparation of Di(tricyclo[5.2.1.0$^{2,6}$]dec-3-en-(8 or 9)-yl Maleate (8).

A 3-1, 4-neck round-bottom flask fitted with a thermometer, 10-plate Oldershaw column, variable rate take-off head, and air inlet/sparge was charged with 1527.5 g of the formate 7, 504 g of methyl maleate, 600 g of toluene, 0.67 g hydroquinone and 9.54 g Tyzor TPT (tetraisopropoxy titanate). Upon adding the Tyzor TPT the solution turned dark brown/red. The take-off head was set to take-off material boiling below 35 C. and the reaction was heated. The reaction refluxed with a pot temperature about 126 C. and a total of 360.8 g of distillate boiling below 35 C. was collected during 9 h reflux. The reaction was heated to 152 C. for an additional 4 h.

Ten ml of water was added to the reaction to hydrolyze the catalyst. The Oldershaw column was removed and the reaction was vacuum distilled to remove excess formate 7 and toluene. A total of 267 g of unreacted 7 was distilled at 99 C./7 mm to about 91 C./1.5 mm.

The residue in the flask was dissolved in some toluene to lower its viscosity and "filtered" on a bed of silica gel in a sintered glass funnel. A black sludge and much of the color was strongly adsorbed on the silica gel to yield a nearly colorless product. The product was concentrated by evaporating the excess toluene on a rotary evaporator (100 C.). The product (1252.5 g) was analyzed by nmr and glpc. It was estimated that the purity was 91%—the major impurities were some residual toluene, 7, and the mixed ester.

9. Sodium Di(tricyclo[5.2.1.0$^{2,6}$]dec-3-en-(8 or 9)-yl sulfosuccinate (9).

The addition of sodium metabisulfite to 8 is completely analogous to Example 3. The product was prepared at 68.2% total solids. The solvent contained 31% isopropanol to give a lower viscosity liquid.

10. Polymerization Efficiency of the Polymerizable Soaps.

In order to evaluate the efficiency of the various soaps in latex preparation, a simple screening procedure was developed. The soaps were used to prepare a low solids polystyrene latex and the rate of polymerization was measured. Upon completion, the particle size was determined by Nanosizer. The rate should follow classical kinetics and the rate (%/min) should be linear in the so-called stage two. The rate and particle size should be indicitive of the efficiency of the soap in generating particles.

GENERAL PROCEDURE

A 1-1, 4-necked, round-bottom flask fitted with stirrer, thermometer, condenser and nitrogen inlet was charged with 350 g double deionized water, 100.0 ml (90 g) styrene monomer, and the desired amount of the particular soap. The control was 0.9 g of siponate DS-10 (1% based on styrene) and other soaps were employed on an equivalent basis to this control). The reaction was sitrred and heated to 50 C. under the nitrogen flow. About 20 min after reaching temperature, a solution of 0.45 g of potassium persulfate in 50 g water was added. The reaction was held at 50 C. and sampled for analysis of the residual styrene by glpc. Time-% styrene plots were evaluated to find the linear stage two region and the rate was computed as % syrene reacting per min. Upon completion, the reaction was filtered and particle size was measured on a Nanosizer. Conversion was measured by solids determination. Data are found in Table 1.

TABLE 1

Particle Size and Rate of Reaction in Styrene Screening Runs
The soaps are described in terms of the two groups attached to the sulfosuccinate moiety (except for the Siponate DS-10 control). For the purpose of this table the tricyclo [5.2.1.0$^{2,6}$]dec-3-en-(8 or 9) oxyethyl alcohol moiety is called DCPOE.

| Soap | % Wt. | Rate (%/min) | Particle Size (nm) | Conversion |
|---|---|---|---|---|
| DS-10 | 1.0 | 0.445 | 99 | 96.3 |
| 2-Ethylhexyl 2-Ethylhexyl | 1.3 | 0.481 | 103 | 97.1 |
| DCPOE Butyl | 1.28 | 0.328 | 128 | 93.5 |
| DCPOE Octyl | 1.46 | 0.457 | 98 | 92.4 |
| DCPOE DCPOE | 1.64 | 0.676 | 86 | 96.3 |
| DCPOE Butyl Carbitol | 1.52 | 0.325 | 134 | 94.9 |
| DCPOE Carbitol | 1.54 | * | 144 | 93.7 |

*Reaction experienced long induction period, then increase in rate. The reaction, as a result was not followed long enough to establish the stage two polymerization.

Conversions do not reflect anything about the soap but merely indicate the point reached when particle size and solids analysis was done.

The rates increase and particle size decreases as the soap becomes more hydrophobic. The DCPOE/Octyl and DCPOE/DCPOE soaps are as good or better than di(2-ethylhexyl)sulfosuccinate or Siponate DS-10 at controlling particle size and rate of reaction in this recipe.

11. Grafting Efficiency of the Tricyclo[5.2.1.0$^{2,6}$]dec-3-enyl Containing Soaps.

The two soaps 4 and 6 were found to hydrolyze in base and when injected into a gc in the presence of water. Therefore, any of the alcohol moiety not grafted to polymer backbone could be easily quantified. To determine the efficiency of attaching the soaps to a latex, a 65 MAA/30 BA/5 MMA latex was prepared by conventional methods using each of the two soaps 4 and 6 at 1% based on total potential polymer solids. To samples of each of these latexes was added 1% of the same soap. These four samples were then hydrolyzed in basic acetone and analyzed for the resulting alcohol 1 and 5. Undecyl alcohol was used as an internal standard. With the unsaturated soap 4, 39% of the possible alcohol was observed in the unspiked sample plus almost all the additional soap spiked into the latex was found in that sample. In the analogous latex made with the saturated soap 6, about 90% of the possible alcohol was found in both the unspiked and spiked latex. These should represent a minimum since only one of the alcohol moieties of the disubstituted surfactants need to be grafted or polymerized to attach the soap, and this leaves the other one free to hydrolyze.

12. Foaming Behaviour of Latexes Made with the Polymerizable Soaps.

A series of latexes made with various soaps, all having approximately the same particle size and composition, were diluted to 15% solids and evaluated for foam height and rate of foam break in a Ross-Miles apparatus. The conventional soap (Alipal CO-436) and three sulfosuccinates: Aerosol OT (di-2-ethylhexyl), Trem LF-40 (allyl, dodecyl), and soap 4 were compared. The sulfosuccinates were the best in terms of rapidity of foam break and the two potentionally polymerizable ones were better then Aerosol OT. Soap 4 was the best of the series.

We claim:

1. A Compound of the formula

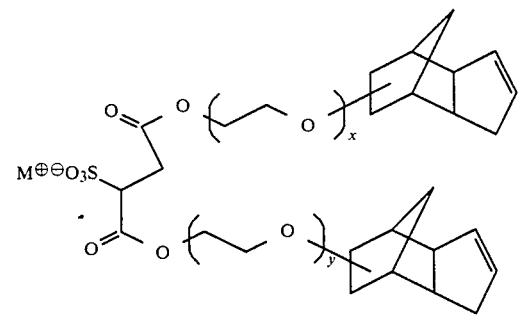

wherein M is a cation selected from the group consisting of alkali metal, ammonium, amino, and hydrogen; and wherein x and y are independently selected from 0 to 2.

2. The compounds of claim 1 wherein M is sodium.

3. The compounds of claim 1 wherein x equals 0, y equals 0 and M equals sodium or ammonium.

4. A compound of the formula

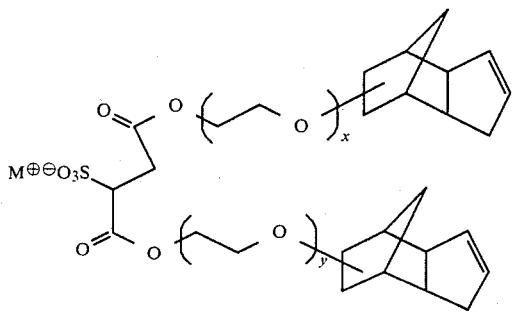
wherein M is a cation selected from the group consisting of alkali metal, ammonium, amino, and hydrogen; and wherein x and y are independently 0 or 1.
* * * * *
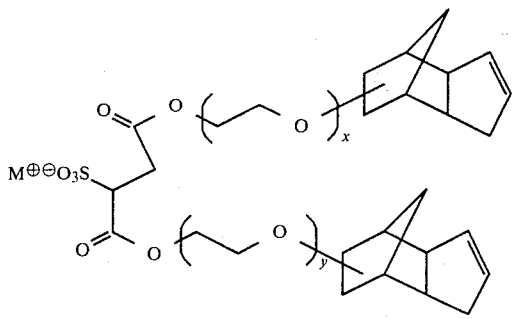
wherein M is a cation selected from the group consisting of alkali metal, ammonium, amino, and hydrogen; and wherein x and y are independently 0 or 1.
* * * * *